United States Patent [19]

Bergmeier et al.

[11] Patent Number: 4,786,648

[45] Date of Patent: Nov. 22, 1988

[54] O-SUBSTITUTED TETRAHYDROPYRIDINE OXIME CHOLINERGIC AGENTS

[75] Inventors: Stephen C. Bergmeier; David A. Downs; Walter H. Moos; David W. Moreland; Haile Tecle, all of Ann Arbor, Mich.

[73] Assignee: Warner-Lambert Company, Morris Plains, N.J.

[21] Appl. No.: 91,893

[22] Filed: Sep. 4, 1987

Related U.S. Application Data

[63] Continuation-in-part of Ser. No. 939,507, Dec. 8, 1986, Pat. No. 4,710,508.

[51] Int. Cl.$^4$ ............... A61K 31/44; C07D 211/70
[52] U.S. Cl. .................................. 514/357; 546/333; 546/334
[58] Field of Search ................ 546/333, 334, 335; 514/357

[56] References Cited

U.S. PATENT DOCUMENTS 4,297,359 10/1981 van Zorge ..................... 546/333

FOREIGN PATENT DOCUMENTS 0239445 9/1987 European Pat. Off. ......... 546/334
0889074 2/1962 United Kingdom ............ 546/334
0511638 1/1976 Japan .............................. 546/334

Primary Examiner—John M. Ford
Assistant Examiner—J. Richter
Attorney, Agent, or Firm—Jerry F. Janssen

[57] ABSTRACT

Certain O-substituted-1,2,5,6-tetrahydro-3- or 1,2,3,6-tetrahydro-4-pyridine oximes are useful as agents for treating pain or for treating the symptoms of senile cognitive decline.

27 Claims, No Drawings

O-SUBSTITUTED TETRAHYDROPYRIDINE OXIME CHOLINERGIC AGENTS

CROSS-REFERENCE TO RELATED APPLICATIONS

This application is a continuation-in-part of Ser. No. 939,507 filed Dec. 8, 1986, now U.S. Pat. No. 4,710,508.

BACKGROUND OF THE INVENTION

The present invention relates to chemical compounds, pharmaceutical compositions, and to a method of treatment employing the compounds and compositions. More particularly, the present invention is concerned with certain O-substituted-1,2,5,6-tetrahydro-3- or 1,2,3,6-tetrahydro-4-pyridine oximes, to pharmaceutical compositions containing these compounds, and to a pharmaceutical method of treatment.

Disorders of cognition are generally characterized by symptoms of forgetfulness, confusion, memory loss, attentional deficits and/or, in some cases, affective disturbances. These symptoms may arise as a result of the general aging process and/or from organic brain disease, cerebrovascular disease, head injury or developmental or genetic defects.

The general decrease in cognitive function which accompanies the aging process is well accepted. The same phenomenon has been observed and documented in many lower mammals, including those routinely employed in pharmacological testing programs for screening and predicting usefulness for particular drugs in higher animals, including humans.

Although disorders of cognition often accompany the general aging process, presenile and senile primary degenerative dementia are the most common accepted causes of mental deterioration in the elderly. It has been estimated that at least ten percent of persons over sixty years of age will eventually suffer severe mental deterioration. A much larger number will experience cognitive decline of sufficient severity to impede their activities.

Many of the symptoms of cognitive disorders, especially impaired memory, are associated with decreased acetylcholine synthesis and the impairment of cholinoreceptive neurons. In the hippocampus and cerebral cortex of patients suffering from primary degenerative dementia for example, the level of the enzyme choline acetyltransferase (CAT) can be reduced by as much as ninety percent. (See Davies, et al, *The Lancet*, 1976 (Vol. 2): 1403; Perry, et al, *J. Neurol. Sci.*, 34:247–265 (1977); and White et al., *The Lancet*, 1977 (Volume 1): 668–670).

Since CAT catalyzes the synthesis of acetylcholine from its precursors choline and acetyl coenzyme A, the loss of CAT reflects the loss of cholinergic, or acetylcholine-releasing, nerve endings in the hippocampus and cerebral cortex. There is abundant evidence that cholinergic terminals in the hippocampus are critically important for memory formation.

The cholinergic hypothesis suggests that drugs which restore acetylcholine levels or which mimic the action of acetylcholine (i.e., are cholinomimetic) are effective in correcting this deficit in neurotransmitter chemical and provide treatment of the memory impairment symptom of cerebral insufficiency. Considerable biochemical, pharmacological, and electrophysiological evidence supports the hypothesis that deficits in the cholinergic system underlie geriatric cognitive dysfunction. (See C. Peterson and G. E. Gibson, *Neurobiol. Aging*, 4: 25–30 (1983)). Aged humans and nonhuman primates with decreased cognition show improved memory when they are treated, for example, with acetylcholinesterase inhibitors such as physostigmine. These agents increase the available supply of synaptic acetylcholine by inhibiting its hydrolysis Aminopyridines such as 3,4-diaminopyridine ameliorate age-related cognitive deficits by increasing the release of acetylcholine from presynaptic nerve terminals, thus increasing synaptic acetylcholine. (See H. P. Davis, et al, *Exp. Aging Res.*, 9: 211–214 (1983)).

It has been known for some time that the natural alkaloid, muscarine, has the ability to act relatively selectively at autonomic effector cells to produce qualitatively the same effects as acetylcholine. Two related alkaloids, pilocarpine and arecoline, have the same principal sites of action as muscarine and acetylcholine and are thus classified as having "muscarinic" action. Although these naturally occurring alkaloids are of great value as pharmacological tools, present clinical use is largely restricted to the use of pilocarpine as a miotic agent.

Arecoline (the methyl ester of 1,2,5,6-tetrahydro-1-methyl-3-pyridinecarboxylic acid) is the chief alkaloid found in betel nuts (*Areca catechu*). Betel nuts have been chewed by natives of the East Indies since early times as a euphoretic. The present pharmaceutical utility of arecoline, however, has been limited to its use as a veterinary anthelmintic agent.

Recently it has been demonstrated that arecoline is effective in ameliorating some of the symptoms of cognitive disorders in patients clinically diagnosed as having presenile primary degenerative dementia. Significant improvement was observed in a test of picture recognition after administration of arecoline to patients in a double blind study. (See Christie, et al, *Brit. J. Psychiatry*, 138: 46–50 (1981)).

Certain 3- or 4-ketoximes of 1-(lower alkyl)1,2,5,6-tetrahydropyridines in which the oxygen is unsubstituted are disclosed in U.S. Pat. No. 3,004,979 and British Patent Specification No. 889,074 as having utility as parasympathomimetic agents acting on nonstriated muscle.

Japanese patent application No. 49-74654 to Tamura, et al, discloses 1-methyl-1,2,5,6-tetrahydro-3-pyridinecarboxaldehyde oxime and its use as a plant growth regulator.

Regarding analgesia, the literature indicates that acetylcholine and muscarine agonists possess antinociceptive activity (see T. T. Chau, et al, *J. Pharmacol. Exp. Ther.*, 222: 612–666 (1982),; W. L. Dewey, et al, *Life Sci.*, 17: 9–10 (1975); and N. W. Pedigo, et al, *Neurosci. Lett.*, 26: 85–90 (1981) and references cited therein).

SUMMARY OF THE INVENTION

The present invention provides, in its broadest chemical compound aspect compounds of Formula I:

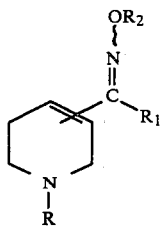

wherein the

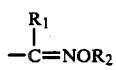

may be attached to the tetrahydropyridine moiety at either carbon atom number three or four of the tetrahydropyridine ring system, and the attachment of the $OR_2$ group to the nitrogen atom is configured either syn- or anti- to the tetrahydropyridine ring.

R is hydrogen or alkyl from one to six carbon atoms, with the provisos that when R is methyl, $R_1$ is hydrogen and when R is ethyl, and $R_1$ is hydrogen, $R_2$ may not be acetyl.

The substituent group $R_1$ is hydrogen; alkyl of from one to six carbon atoms optionally substituted with hydroxy or alkoxyl of from one to four carbon atoms; alkenyl of from one to six carbon atoms optionally substituted with hydroxy or alkoxyl of from one to four carbon atoms; alkynyl of from one to six carbon atoms optionally substituted with hydroxy or alkoxyl of from one to four carbon atoms; cycloalkyl of from three to eight carbon atoms;

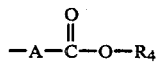

where A is a bond or is a hydrocarbon chain of from one to four carbon atoms and when containing two or more carbon atoms may contain one double bond and where $R_4$ is alkyl of from one to six carbon atoms;

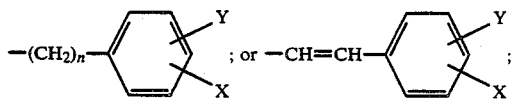

where n is zero to four and X and Y are independently selected from hydrogen, fluorine, chlorine, bromine, hydroxy, straight or branched alkyl of from one to three carbon atoms, or alkoxyl of from one to four carbon atoms.

$R_2$ is selected from alkyl of from one to six carbon atoms optionally substituted with hydroxy or alkoxyl of from one to four carbon atoms; alkenyl of from one to six carbon atoms optionally substituted with hydroxy or alkoxyl of from one to four carbon atoms; alkynyl of from one to six carbon atoms optionally substituted with hydroxy or alkoxyl of from one to four carbon atoms; cycloalkyl of from three to six carbon atoms; or

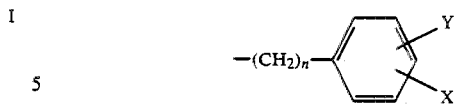

where n is zero to four and X and Y are independently selected from hydrogen, fluorine, chlorine, bromine, hydroxy, alkyl of from one to three carbon atoms, or alkoxyl of from one to four carbon atoms; alkylcarbonyl of from two to twelve carbon atoms; alkenylcarbonyl of from three to twelve carbon atoms; alkynylcarbonyl of from three to twelve carbon atoms;

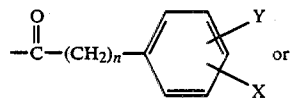 or

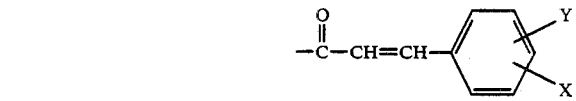

where n, X and Y are as previously defined; or

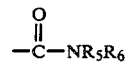

where $R_5$ and $R_6$ are independently selected from hydrogen, alkyl of from one to four carbon atoms or phenyl; or a pharmaceutically acceptable acid addition salt thereof.

In another aspect, the present invention provides pharmaceutical compositions useful as analgesic agents comprising an analgesically effective amount of a compound as defined above in combination with a pharmaceutically acceptable carrier.

In another aspect, the present invention provides pharmaceutical compositions for treating the symptoms of senile cognitive decline comprising a cholinergically effective amount of a compound as defined above in combination with a pharmaceutically acceptable carrier.

In another aspect, the present invention provides a method of alleviating pain in a mammal comprising administering to a mammal in need of such treatment an analgesically effective amount of a compound as defined above in combination with a pharmaceutically acceptable carrier.

In yet another aspect, the present invention provides a method of treating the symptoms of senile cognitive decline in the elderly characterized by decreased cerebral acetylcholine production or release comprising administering to a patient in need of such treatment a cholinergically effective amount of a compound as defined above in combination with a pharmaceutically acceptable carrier.

DETAILED DESCRIPTION

The compounds of the present invention comprise a class of O-substituted 1,2,5,6-tetrahydro-3- or 1,2,3,6-tetrahydro-4-pyridine oximes and their pharmaceutically acceptable salts which are centrally acting muscarinic agents and which are thus useful as analgesic agents, sleep aids, or therapeutic agents for treating the symptoms of senile dementia, Alzheimer's disease, Huntington's chorea, tardive dyskinesia, hyperkinesia, mania or similar conditions of cerebral insufficiency characterized by decreased cerebral acetylcholine production or release.

The substituent R in the compounds of this invention is hydrogen or alkyl of from one to six carbon atoms, with the provisos that when R is methyl, $R_1$ hydrogen and when R is ethyl and $R_1$ is hydrogen, $R_2$ may not be acetyl. 1-Ethyl-1,2,5,6- tetrahydro-3-pyridinecarboxaldehyde, O-acetyl oxime is disclosed in Wohl, et al, Ber., 38: (4167). Compounds in which R is methyl and $R_1$ is other than hydrogen are disclosed in the parent of this application, U.S. Ser. No. 939,507 filed Dec. 8, 1986.

The substituent group $R_1$ in structural Formula I above is selected from hydrogen; alkyl of from one to six carbon atoms optionally substituted with hydroxy or alkoxyl of from one to four carbon atoms; alkenyl of from one to six carbon atoms optionally substituted with hydroxy or alkoxyl of from one to four carbon atoms; alkynyl of from one to six carbon atoms optionally substituted with hydroxy or alkoxyl of from one to four carbon atoms; cycloalkyl of from three to eight carbon atoms;

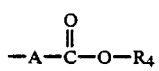

where A is a bond or a hydrocarbon chain of from zero to four carbon atoms and when containing two or more carbon atoms may contain one double bond and $R_4$ is alkyl of from one to six carbon atoms; or carbon atoms; or

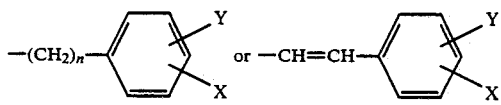

where n is zero to four and X and Y are independently selected from hydrogen, fluorine, chlorine, bromine, hydroxy, straight or branched alkyl of from one to three carbon atoms, or alkoxyl of from one to four carbon atoms.

In compounds of the present invention, the substituent group $R_2$ is selected from alkyl of from one to six carbon atoms optionally substituted with hydroxy or alkoxyl of from one to four carbon atoms; alkenyl of from one to six carbon atoms optionally substituted with hydroxy or alkoxyl of from one to four carbon atoms; alkynyl of from one to six carbon atoms optionally substituted with hydroxy or alkoxyl of from one to four carbon atoms; cycloalkyl of from three to six carbon atoms; or

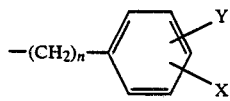

where n is zero to four and X and Y are independently selected from hydrogen, fluorine, chlorine, bromine, hydroxy, alkyl of from one to three carbon atoms, or alkoxyl of from one to four carbon atoms; alkylcarbonyl of from two to twelve carbon atoms; alkenylcarbonyl of from three to twelve carbon atoms; alkynylcarbonyl of from three to twelve carbon atoms;

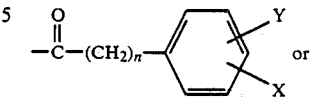

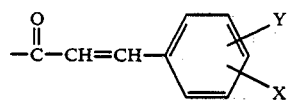

where n, X and Y are as previously defined; or

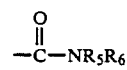

where $R_5$ and $R_6$ are independently selected from hydrogen, alkyl of from one to four carbons, and phenyl.

The term "alkyl of from one to six carbon atoms" denotes a substituent group derived from a saturated hydrocarbon by removal of a single hydrogen atom. The term includes methyl, ethyl, n-propyl, iso-propyl, n-butyl, sec-butyl, iso-butyl, tert-butyl, and the various isomeric forms of pentyl and hexyl. Likewise, the terms "alkenyl of from one to six carbon atoms" and "alkynyl of from one to six carbon atoms" denote substituent groups derived, respectively, from alkene or alkyne hydrocarbons by the removal of a single hydrogen atom. These terms include ethenyl, ethynyl, propenyl, propynyl, and similar branched and unbranched unsaturated hydrocarbon groups of up to six carbon atoms.

The term "cycloalkyl of from three to eight carbon atoms" denotes saturated carbocyclic rings such as cyclopropyl, cyclobutyl, cyclopentyl, cyclohexyl, as well as alkyl substituted carbocyclic rings containing up to eight carbon atoms such as methyl-, dimethyl-, and ethylcyclohexyl.

The terms "alkoxy" or "alkoxyl" denote a substituent group derived by removal of the hydrogen from the oxygen atom of a saturated alcohol and attached to the parent molecular moiety through the oxygen atom. Such groups include methoxyl, ethoxyl, 1- and 2-propoxyl, and similar branched and unbranched alkoxyl groups of up to four carbon atoms.

The terms "alkylcarbonyl," "alkenylcarbonyl," and "alkynylcarbonyl" denote substituent alkyl, alkenyl, or alkynyl groups as previously defined, attached to the parent molecular moiety through a carbonyl group.

The compounds of the present invention may exist in either of two isomeric forms in which the oxygen atom of the oxime group and its attached substituent, $R_2$, may be either syn- or anti- with respect to the tetrahydropyridine ring. The present invention includes both forms of the compounds as well as mixtures of the syn- and anti- forms. Moreover, in those compounds in which there is a double bond in a carbon chain, both the Z (i.e. cis-) and E (i.e. trans) forms are included in the present invention. The terms syn- and anti- as they apply to the compounds of the present invention are illustrated by Formulas Ia and Ib:

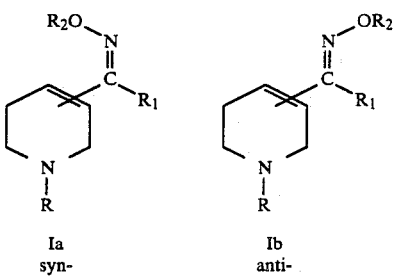

Ia syn-    Ib anti-

Examples of compounds contemplated as falling within the scope of the present invention include, but are not limited to the following:

1,2,5,6-Tetrahydro-3-pyridinecarboxaldehyde, O-methyloxime.
1,2,5,6-Tetrahydro-3-pyridinecarboxaldehyde, O-ethyloxime.
1-(1,2,5,6-Tetrahydro-3-pyridinyl)ethanone, O-methyloxime.
1-(1,2,5,6-Tetrahydro-3-pyridinyl)-1-propanone, O-methyloxime.
1,2,5,6-Tetrahydro-1-methyl-3-pyridinecarboxaldehyde, O-methyloxime.
1,2,5,6-Tetrahydro-1-methyl-3-pyridinecarboxaldehyde, O-ethyloxime.
1,2,5,6-Tetrahydro-1-ethyl-3-pyridinecarboxaldehyde, O-methyloxime.
1,2,3,6-Tetrahydro-4-pyridinecarboxaldehyde, O-methyloxime.
1-(1,2,3,6-Tetrahydro-4-pyridinyl)ethanone, O-methyloxime.
1,2,3,6-Tetrahydro-1-methyl-4-pyridinecarboxaldehyde, O-methyloxime.
1,2,3,6-Tetrahydro-1-methyl-4-pyridinecarboxaldehyde, O-acetyl oxime.

Compounds of the present invention are prepared by the general synthetic method detailed in Reaction Sequence 1, following.

Referring to Reaction Sequence 1, the desired starting 3- or 4-ketopyridine or 3-, or 4-pyridinecarboxaldehyde, 1, is first converted to the corresponding oxime or O-substituted oxime, 2, by the action of hydroxylamine hydrochloride or O-substituted hydroxylamine hydrochloride. The oxime, or substituted oxime, 2, is reacted with the desired lower alkyl halide to produce the N-alkylpyridinium oximes, 3. These pyridinium salts are reduced by the action of sodium borohydride, generally in a mixed water/alcohol medium at ambient temperature, to produce the substituted 3- or 4-oximino-1,2,5,6-tetrahydropyridine compounds, 4, of the present invention. If desired, these oximes, 4, may be further converted to the N,N-dialkyltetrahydropyridinium halide salts by reaction with the desired alkyl halide by conventional means.

Reaction Sequence 1

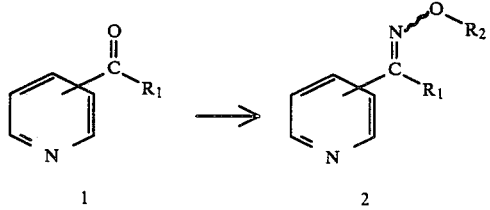

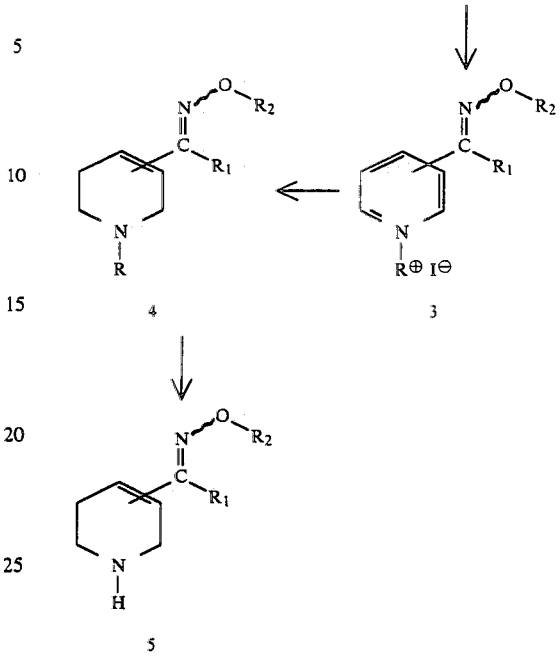

If the desired product is a compound where R is hydrogen, the N-alkyl tetrahydropyridine oxime, 4, is reacted with 1-chloroethyl chloroformate to produce compound 5.

By virtue of the basic nitrogen atom in the tetrahydropyridine ring, the compounds of the present invention form pharmaceutically acceptable acid addition salts with organic and inorganic acids. Examples of suitable acids for the formation of pharmaceutically acceptable salts are hydrochloric, sulfuric, phosphoric, acetic, benzoic, citric, malonic, salicylic, malic, fumaric, oxalic, succinic, tartaric, lactic, gluconic, ascorbic, maleic, aspartic, benzenesulfonic, methane-and ethanesulfonic, hydroxymethane- and hydroxyethanesulfonic, and the like. (See for example, "Pharmaceutical Salts," J. Pharm. Sci., 66 (1): 1-19 (1977)).

In a similar manner, the N,N-lower dialkyl tetrahydropyridinium salts may be used in the pharmaceutical method of this invention as, for example, the N,N-dimethyl-tetrahydropyridinium halide salts.

The salts are prepared by contacting the free base form of the compounds of this invention with a sufficient amount of the desired acid or alkyl halide to produce the salt in the conventional manner. The free base forms may be regenerated, if desired, by treating the salt form with a base. For example, dilute aqueous solutions of such bases as sodium hydroxide, potassium carbonate, ammonia, and sodium bicarbonate may be utilized for this purpose.

The free base forms of the compounds of this invention differ somewhat from their respective salt forms in such physical properties as melting point and solubility in polar solvents, but the salts are otherwise equivalent to their respective free base forms for the purposes of the invention.

The compounds of the present invention are muscarinic agents and are thus useful as analgesic agents for the treatment of pain in mammals including man, as sleep aids, and as agents for treating the symptoms of senile dementia, Alzheimer's disease, Huntington's chorea, tardive dyskinesia, hyperkinesia, mania or similar conditions of cerebral insufficiency characterized by decreased cerebral acetylcholine production or release.

The biological activity of compounds of the present invention was evaluated using a number of tests. The activity of compounds of this invention as central muscarinic binding site agonists and antagonists was measured. In the RQNB screening assay, which is described more fully by Mark Watson, et al, *J. Pharmacol. Exp. Ther.*, 237 (2): 411 (1986), rat cerebral cortex tissue was treated with radio-labeled quinuclidinyl benzilate, a known muscarinic binding site antagonist. The concentrations of test compound required to inhibit 50% of the binding of this muscarinic antagonist were then determined.

Similarly, in the RCMD screening assay, described more fully by T. W. Vickeroy, et al, *J. Pharmacol. Exp. Ther.*, 229 (3): 747 (1984), rat cerebral cortex tissue was treated with radio-labeled cis-methyldioxolane, a known muscarinic binding site agonist. The concentrations of test compounds required to inhibit 50% of the binding of this muscarinic agonist were then determined. These values are reported as $IC_{50}$ concentrations in Tables 1 and 2 and demonstrate that the compounds of the present invention possess significant muscarinic activity.

In a second screening assay, designated SIS, the scopolamine induced swimming test, the ability of representative compounds of the present invention to reverse the hyperactive swimming behavior of laboratory rats given scopolamine was assessed. In this test, untreated rats will generally swim between 20 to 30 meters during a five minute test period. Rats given scopolamine at does of 0.1 mg/kg develop a stereotypical swimming hyperactivity with the swimming distances generally increasing by 75–125% above baseline values. This swimming hyperactivity can be reversed by administration of physostigmine or the cholinergic agonist, arecoline. The effect of scopolamine is centrally mediated; the ability of a test compound to reverse the hyperactive swimming behavior induced by scopolamine is thus a measure of the central cholinergic activity of the compound.

The minimal effective dose (MED) for several representative compounds of this invention required to demonstrate reversal of the scopolamine-induced hyperactive swimming activity in laboratory rats is presented in Tables 3 and 4.

TABLE 1

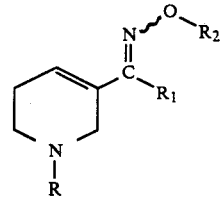

| R | $R_1$ | $R_2$ | $IC_{50}$ (Micromolar) RQNB | RCMD |
|---|---|---|---|---|
| Hydrogen | Ethyl | Methyl | 9.5 | 0.29 |
| Methyl | Hydrogen | Methyl | 1.8 | 0.002 |
| Hydrogen | Hydrogen | Methyl | 7.1 | 0.01 |
| Methyl | Hydrogen | Ethyl | 10.0 | 0.028 |
| Hydrogen | Hydrogen | Ethyl | 1.0 | 0.042 |

TABLE 1-continued

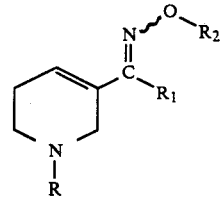

| R | $R_1$ | $R_2$ | $IC_{50}$ (Micromolar) RQNB | RCMD |
|---|---|---|---|---|
| Hydrogen | Methyl | Methyl | 5.8 | 0.028 |

TABLE 2

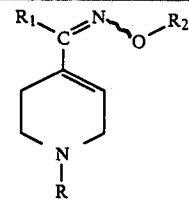

| R | $R_1$ | $R_2$ | $IC_{50}$ (Nanomolar) RQNB | RCMD |
|---|---|---|---|---|
| Methyl | Hydrogen | Methyl | >1.0 | >0.1 |
| Hydrogen | Hydrogen | Methyl | <1.0 | >0.1 |

TABLE 3

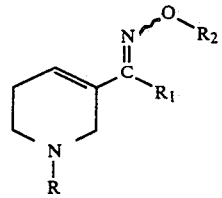

| R | $R_1$ | $R_2$ | Minimal Effective Dose (mg/kg) (Subcutaneous) for Reversal of Scopolamine-Induced Swimming Hyperactivity |
|---|---|---|---|
| Methyl | Hydrogen | Methyl | 3.2 |
| Hydrogen | Hydrogen | Methyl | 3.2 |

TABLE 4

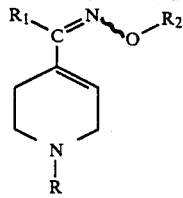

| R | $R_1$ | $R_2$ | Minimal Effective Dose (mg/kg) (Subcutaneous) for Reversal of Scopolamine-Induced Swimming Hyperactivity |
|---|---|---|---|
| Hydrogen | Methyl | Methyl | 10 |
| Methyl | Hydrogen | Methyl | 32 |

In therapeutic use as agents for treating pain or for treating cerebral insufficiency, the compounds utilized in the pharmaceutical method of this invention are administered to the patient at dosage levels of from 0.007 to 7000 mg per day. For a normal human adult of approximately 70 kg of body weight, this translates into a dosage of from 0.0001 to 100 mg/kg of body weight per day. The specific dosages employed, however, may be varied depending upon the requirements of the patient, the severity of the condition being treated, and the activity of the compound being employed. The determination of optimum dosages for a particular situation is within the skill of the art.

For preparing pharmaceutical compositions from the compounds of this invention, inert, pharmaceutically acceptable carriers can be either solid or liquid. Solid form preparations include powders, tablets, dispersable granules, capsules, cachets, and suppositories.

A solid carrier can be one or more substances which may also act as diluents, flavoring agents, solubilizers, lubricants, suspending agents, binders, or tablet disintegrating agents; it can also be an encapsulating material.

In powders, the carrier is a finely divided solid which is in a mixture with the finely divided active component. In tablets, the active compound is mixed with the carrier having the necessary binding properties in suitable proportions and compacted in the shape and size desired.

For preparing suppositories, a low-melting wax such as a mixture of fatty acid glycerides and cocoa butter is first melted, and the active ingredient is dispersed therein by, for example, stirring. The molten homogeneous mixture is then poured into convenient sized molds and allowed to cool and solidify.

Powders and tablets preferably contain between about 5 to about 70% by weight of the active ingredient. Suitable carriers are magnesium carbonate, magnesium stearate, talc, lactose, sugar, pectin, dextrin, starch, tragacanth, methyl cellulose, sodium carboxymethyl cellulose, a low-melting wax, cocoa butter, and the like.

The term "preparation" is intended to include the formulation of the active compound with encapsulating material as a carrier providing a capsule in which the active component (with or without other carriers) is surrounded by a carrier, which is thus in association with it. In a similar manner, cachets are also included.

Tablets, powders, cachets, and capsules can be used as solid dosage forms suitable for oral administration.

Liquid form preparations include solutions suitable for oral or parenteral administration, or suspensions, and emulsions suitable for oral administration. Sterile water solutions of the active component or sterile solutions of the active component in solvents comprising water, ethanol, or propylene glycol may be mentioned as examples of liquid preparations suitable for parenteral administration.

Sterile solutions may be prepared by dissolving the active component in the desired solvent system, and then passing the resulting solution through a membrane filter to sterilize it or, alternatively, by dissolving the sterile compound in a previously sterilized solvent under sterile conditions.

Aqueous solutions for oral administration can be prepared by dissolving the active compound in water and adding suitable flavorants, coloring agents, stabilizers, and thickening agents as desired. Aqueous suspensions for oral use can be made by dispersing the finely divided active component in water together with a viscous material such as natural or synthetic gums, resins, methyl cellulose, sodium carboxymethyl cellulose, and other suspending agents known to the pharmaceutical formulation art.

Preferably, the pharmaceutical preparation is in unit dosage form. In such form, the preparation is divided into unit doses containing appropriate quantities of the active component. The unit dosage form can be a packaged preparation, the package containing discrete quantities of the preparation, for example, packeted tablets, capsules, and powders in vials or ampoules. The unit dosage form can also be a capsule, cachet, or tablet itself, or it can be the appropriate number of any of these packaged forms.

The compounds of the present invention may also be co-administered when desired with anticholinergic agents, for example, atropine, methylatropine, glycopyrrolate, scopolamine, methylscopolamine, pirenzepine, and AF-DX-116, to reduce cholinergic side-effects.

The following preparative examples are provided to enable one skilled in the art to practice the invention. They are illustrative of the present invention and are not to be read as limiting the scope of the invention as it is defined by the appended claims.

EXAMPLE 1

Preparation of 1,2,5,6-Tetrahydro-1-methyl-3-pyridinecarboxaldehyde, oxime

Step 1 —Preparation of 3-Pyridine aldoxime

3-Pyridine carboxaldehyde (21.4 g, 200 mmol) and hydroxylamine hydrochloride (14.6 g, 210 mmol) were dissolved in $CH_3OH$ (125 ml) and heated at reflux for 12 hours. The solution was then concentrated under vacuum to give a white solid. To this solid was added saturated $NaHCO_3$ solution, with stirring until slightly basic. A white precipitate was obtained which was filtered, washed with water, and dried in vacuo, to give 3-pyridine aldoxime as a white solid, 23.6 g, 97% yield, mp 148°–150° C.

Step 2 —Preparation of 1-(3-Pyridinyl)aldoxime methiodide

3-Pyridine aldoxime (23.6 g, 194 mmol) was suspended in EtOAc (300 ml), methyliodide (23 ml, 370 mmol) was added, and the mixture was heated at reflux for three hours. The reaction was then cooled in an ice bath, filtered, washed with $Et_2O$ and dried in vacuo to give 42.7 g of 1-(3-pyridinyl)-aldoxime methiodide as a tan solid, 83% yield, mp 178°–182° C., elemental analysis within theory ($\pm 0.4\%$) for $C_7H_9N_2OI$.

Step 3 —Preparation of 1,2,5,6-Tetrahydro-1-methyl-3-pyridinecarboxaldehyde, oxime, monohydrochloride The methiodide (42.7 g, 162 mmol) was dissolved in $CH_3OH$-$H_2O$ (250 ml, 1:1) and added to an ice cooled solution of $NaBH_4$ (11.2 g, 296 mmol) in $CH_3OH$-$H_2O$ (250 ml, 1:1). After the addition was complete, the reaction was warmed to room temperature over one hour. Water (400 ml) was added and the reaction was extracted with $CHCl_3$ (3×250 ml). The combined organic extracts were dried over $MgSO_4$, filtered, and concentrated in vacuo to give a dark oil. This was immediately chromatographed on silica gel, eluting with 10% $CH_3OH$, 90% $CHCl_3$. The HCl salt was then prepared in Et$_2$O to give 1.9 g of 3-pyridinecarboxaldehyde, 1,2,5,6-tetrahydro-1-methyl-, oxime, monohydrochloride as an offwhite solid, 6.7% yield, mp 249–251° C., elemental analysis within theory (±0.4%) for C$_7$H$_{12}$N$_2$O.HCl.

EXAMPLE 2

Preparation of
1-(1,2,5,6-Tetrahydro-3-pyridinyl)-1-propanone, O-Methyloxime 1-(1,2,5,6-Tetrahydro-1-methyl-3-pyridinyl)propanone, O-methyloxime (8.8 g, 48 mmol) was dissolved in CH$_2$Cl$_2$ (50 ml) under N$_2$ and cooled in an ice bath. To this solution was added 1-chloroethyl chloroformate (7.2 g, 50 mmol). The reaction mixture was warmed to room temperature and stirred for four hours. The solvent was then removed under vacuum to give a sticky oil to which was added CH$_3$OH (100 ml) and the solution was heated to reflux for one hour, then stirred at room temperature overnight. The solvent was removed under vacuum to give a brown solid. Acetone (100 ml) was added and a white solid separated and was filtered, washed with Et$_2$O, and dried in vacuo. 5.8 g of 1-propanone, 1-(1,2,5,6-tetrahydro-3-pyridinyl)-, O-methyloxime, monohydrochloride was obtained as a white solid, 59% Yield, mp 209°–210°, elemental analysis within theory (±0.4%) for C$_9$H$_{16}$N$_2$O.HCl.

EXAMPLE 3

Preparation of
1,2,5,6-Tetrahydro-1-methyl-3-pyridinecarboxaldehyde O-Methyloxime Step 1—Preparation of 3-Pyridinecarboxaldehyde, O-Methyl oxime 3-Pyridinecarboxaldehyde (100 g, 934 mmol) and methoxyamine hydrochloride (85.8 g, 102.7 mmol) were dissolved in CH$_3$OH (700 ml) and heated at reflux overnight. The solvent was removed under vacuum to give a white solid. Ten percent aqueous Na$_2$CO$_3$ was added until the solution was basic. The aqueous solution was extracted with EtOAc (3×500 ml). The combined organic extracts were dried over MgSO$_4$, filtered, and the solvent removed under vacuum to give a clear yellow liquid 123.5 g, 97% yield, elemental analysis within theory (±0.4%) for C$_7$H$_8$N$_2$O.

Step 2—Preparation of 3-[(Methoxyimino)methyl]-1-methylpyridinium iodide

3-Pyridinecarboxaldehyde, O-methyloxime (118.5 g, 871 mmol) was dissolved in EtOAc (1500 ml) in a 3L flask fitted with a mechanical stirrer. CH$_3$I (108 ml, 1741 mmole) was added and the reaction heated at reflux for two hours. The reaction was cooled to room temperature, Et$_2$O (1000 ml) was added and the yellow solid was filtered and washed with Et$_2$O (1000 ml) then dried in vacuo to give pyridinium-3-[(methoxyimino)methyl]-1-methyliodide as a yellow solid, 210.6 g, 87% yield, mp 159°–161° C., elemental analysis within theory (±0.4%) for C$_8$H$_{11}$N$_2$OI.

Step 3—Preparation of 1,2,5,6-Tetrahydro-1-methyl-3-pyridinecarboxaldehyde, O-Methyl oxime Pyridinium-3-[(methoxyimino)methyl]-1-methyliodide (100 g, 360 mmol) was dissolved in CH$_3$OH-H$_2$O (700 ml, 1:1) and slowly added to an ice cooled solution of NaBH$_4$ (27.3 g, 720 mmol) in CH$_3$OH-H$_2$O (300 ml, 1:1). After the addition was complete, the reaction was allowed to warm to room temperature and then extracted with CHCL$_3$ (3×400 ml). The combined organic extracts were dried over MgSO$_4$, filtered, and the solvent removed under vacuum to give a red liquid which was distilled with the major fraction boiling at 52°–55° C./0.25 mmHg to give 36.4 g of 3-pyridinecarboxaldehyde-1,2,5,6-tetrahydro-1-methyl-O-methyloxime as a yellow liquid, 66% yield, elemental analysis for C$_8$H$_{14}$N$_2$O. The monohydrochloride was prepared in Et$_2$O with HCl gas to give a white solid, mp 218°–219° C., elemental analysis within theory (±0.4%) for C$_8$H$_{14}$N$_2$O.HCl.

EXAMPLE 4

Preparation of
1,2,5,6-Tetrahydro-3-pyridinecarboxaldehyde, O-Methyl oxime

3-Pyridine carboxaldehyde-1,2,5,6-tetrahydro-1-methyl-O-methyloxime (10.8 g, 70 mmol) was dissolved in CH$_2$Cl$_2$ (70 ml) under N$_2$ and cooled in an ice bath. 1-Chloroethyl chloroformate (7.9 ml, 73 mmol) was added to this solution and the reaction was warmed to room temperature and stirred for four hours. The solvent was removed under vacuum and CH$_3$OH (100 ml) was added to the residue. This solution was heated at reflux for one hour and then stirred at room temperature overnight. The solvent was removed under vacuum to give a brown solid. Addition of acetone (~100 ml) provided a white solid which was filtered, washed with Et$_2$O and dried in vacuo to give 8.1 g of 3-pyridinecarboxaldehyde-1,2,5,6-tetrahydro-O-methyloxime monohydrochloride as an off white solid, 66% yield, mp 205°–207° C., elemental analysis within theory (±0.4%) for C$_7$H$_{12}$N$_2$O.HCL.

EXAMPLE 5

Preparation of
1,2,5,6-Tetrahydro-1-ethyl-3-pyridinecarboxaldehyde, O-Methyl oxime Step 1—Preparation of 3-[(Oximino)methyl]-1-ethylpyridinium iodide 3-Pyridine aldoxime (12.2 g, 100 mmol, Aldrich) was dissolved in EtOAc (200 ml) and EtI (30 ml, 375 mmol) was added. The reaction was heated at reflux for 18 hours, cooled to room temperature, diluted with Et$_2$O and the yellow solid filtered, rinsed with Et$_2$O, and dried in vacuo. 19.9 g of pyridinium-3-[(oximino)methyl]-1-ethyl iodide was obtained as a pale yellow powder, 72% yield.

Step 2—Preparation of 1,2,5,6-Tetrahydro-1-ethyl-3-pyridinecarboxaldehyde oxime

Pyridinium-3-[(oximino)methyl]-1-ethyl iodide (19.9 g, 72 mmol) was dissolved in CH$_3$OH-H$_2$O (70 ml, 1:1) and added to an ice cooled solution of NaBH$_4$ (5.5 g, 144 mmol) in CH$_3$OH-H$_2$O (140 ml, 1:1). After the addition was complete, the reaction was warmed to room temperature and the solvent removed under vacuum. The residue was dissolved in water (~100 ml) and extracted with CHCl$_3$ (3×100 ml).

The combined organic extracts were dried over MgSO$_4$, filtered, the solvent removed under vacuum, and the residue chromatographed (silica gel, gradient elution with CHCl$_3$ increasing to 10% CH$_3$OH-90%

CHCl₃). The HCl salt was prepared in EtOH to give 5.6 g of 3-pyridine carboxaldehyde-1,2,5,6-tetrahydro-1-ethyloxime, monohydrochloride as white needles, 41% yield, mp 232°–233° C., elemental analysis within theory (±0.4%) for $C_8H_{14}N_2O \cdot HCl$.

Step 3—Preparation of 3-[(Methoxyimino)methyl]-1-ethylpyridinium iodide

Pyridinecarboxaldehyde-O-methyloxime (10.0 g, 73.5 mmol) was dissolved in EtOAc (100 ml) and ethyliodide (33 g, 210 mmol) was added. The reaction was heated at reflux for eight hours then stirred at room temperature for two days. The yellow solid was filtered, washed with Et₂O, and dried in vacuo to give 17.8 g of pyridinium-3-[(methoxyimino)methyl]-1-ethyliodide as a yellow powder, 83% yield, mp 113°–116° C., elemental analysis within theory (±0.4%) for $C_9H_{13}N_2OI$.

Step 4—Preparation of 1,2,5,6-Tetrahydro-1-ethyl-3pyridinecarboxaldehyde, O-methyl oxime Pyridinium-3-[(methoxyimino)methyl]-1-ethyliodide (17.8 g, 61 mmol) was dissolved in CH₃OH-H₂O (60 ml, 1:1), and slowly added to an ice cooled solution of NaBH₄ (4.6 g, 122 mmol) in CH₃OH-H₂O (10 ml, 1:1). After the addition was complete, the ice bath was removed and the reaction stirred for two hours and then extracted with CHCl₃ (3×100 ml). The combined organic extracts were dried over MgSO₄, filtered, and the solvent removed. The residue was chromatographed on silica gel and eluted with 5% CH₃OH-95% CHCl₃. The HCl salt was then prepared in EtOH to provide 5.7 g of 3-pyridinecarboxaldehyde-1,2,5,6-tetrahydro-1-ethyl-O-methyloxime, monohydrochloride as a white powder, 45% yield, mp 219°–220° C., elemental analysis within theory (±0.4%) for $C_9H_{16}N_2O \cdot HCL$.

EXAMPLE 6

Preparation of 1,2,5,6-Tetrahydro-1-methyl-3-pyridinecarboxaldehyde, O-Ethyloxime

Step 1—Preparation of 3-Pyridine carboxaldehyde, O-ethyloxime

3-Pyridinecarboxaldehyde (10.7, 100 mmol) and ethoxyamine, hydrochloride (10 g, 102.5 mmol) were dissolved in CH₃OH (100 ml) and heated at reflux for three hours. The solvent was removed under vacuum and 10% aqueous Na₂CO₃ solution was added to the residue until the solution remained basic. The aqueous solution was extracted with EtOAc (3×100 ml), dried over MgSO₄, filtered, and the solvent removed under vacuum. 13.2 g of 3-pyridinecarboxaldehyde-O-ethyloxime as a clear liquid was obtained 88% yield.

Step 2—Preparation of 3-[(Ethoxyimino)methyl]-1-methylpyridinium iodide

3-Pyridinecarboxaldehyde-O-ethyloxime (13.2 g, 88 mmol) was dissolved in EtOAc (200 ml). After the addition of methyliodide (20 g, 180 mmol), the reaction mixture was heated at reflux for two hours, then cooled to room temperature, diluted with Et₂O, and filtered. The resulting yellow solid was washed with Et₂O and dried in vacuo to give pyridinium-3-[(ethoxyimino)methyl]-1-methyliodide as a yellow powder, 25.4 g, 99% yield.

Step 3—Preparation of 1,2,5,6-Tetrahydro-1-methyl-3-pyridinecarboxaldehyde, O-ethyloxime Pyridinium-3-[(ethoxyimino)methyl]-1-methyliodide (25.4 g, 86.9 mmol) was dissolved in CH₃OH-H₂O (80 ml, 1:1) and slowly added to an ice cooled solution of NaBH₄ (6.6 g, 174 mmol) in CH₃OH-H₂O (80 ml, 1:1). The reaction mixture was then warmed to room temperature and extracted with CHCl₃ (3×100 ml). The combined organic layers were dried over MgSO₄, filtered, and the solvent removed under vacuum. The residue was chromatographed on silica gel and eluted with 4% CH₃OH-96% CHCl₃. 9.5 g of 3-pyridinecarboxaldehyde-1,2,5,6-tetrahydro-1-methyl-O-ethyloxime was obtained as a clear oil, 65% yield. This was converted to the monohydrochloride salt in Et₂O, mp 197°–198° C., elemental analysis within theory (±0.4%) for $C_9H_{16}N_2O \cdot HCl$.

EXAMPLE 7

Preparation of 1,2,5,6-Tetrahydro-3-pvridinecarboxaldehyde, O-Ethyloxime

3-Pyridinecarboxaldehyde-1,2,5,6-tetrahydro-1-methyl-O-ethyloxime (4.9 g, 24 mmol) was dissolved in CH₂Cl₂ (50 ml) under N₂ and cooled in an ice bath. 1-Chloroethyl chloroformate (3.5 ml, 32 mmol) was added, the ice bath was removed, and the reaction was stirred for four hours. The solvent was removed under vacuum and the residue dissolved in CH₃OH (50 ml). This solution was heated at reflux for two hours and then stirred at room temperature overnight. The solvent was removed under vacuum to give a brown solid, acetone (~100 ml) was added and the resulting white powder was filtered, rinsed with Et₂O and dried in vacuo to give 3.2 g of 3-pyridinecarboxaldehyde-1,2,5,6-tetrahydro-O-ethyloxime, monohydrochloride as a tan powder, 58% yield, mp 200°–201° C., elemental analysis within theory (±0.4%) for $C_8H_{14}N_2O \cdot HCl$.

EXAMPLE 8

Preparation of 1-(1,2,5,6-Tetrhahydro-3-pyridinyl)ethanone, O-Methyloxime

To an ice cold solution of the N-methylamine (9.3 g, 0.06 mol) in CH₂Cl₂ (150 ml) was added dropwise 1-chloroethyl chloroformate (9.6 g, 0.6 mol). After stirring for 15 minutes at 0° C., the solution was allowed to warm to room temperature and stirred an additional hour. The solvent was removed under reduced pressure and replaced with methanol (150 ml). The solution was heated at reflux for one hour and after cooling concentrated under reduced pressure. The resulting gummy solid was triturated with isopropyl ether to give a white solid, mp 189°–191° C.

Calc: C, 50.39; H, 7.93; N, 14.69; Found: C, 50.50; H, 7.82; N, 14.57.

EXAMPLE 9

Preparation of 1,2,3,6-Tetrahydro-1-methyl-4-pyridinecarboxaldehyde, oxime

Step 1—Preparation of 4-Pyridinecarboxaldehyde oxime

A solution of 4-pyridine carboxaldehyde (25.0 g, 233 mmol) in 100 ml of methanol was treated with hydroxylamine hydrochloride (17.84 g, 250 mmol) and stirred 15 minutes at room temperature. The resulting white solid was collected by filtration and dried in vacuo to provide 27.0 g of 4-pyridine carboxaldehyde oxime, hydrochloride, mp 246°-247° C.

Analysis calculated for $C_6H_6N_2O\cdot HCl$ (158.60): C, 45.44; H, 4.45; N, 17.67; Cl, 22.36; Found: C,45.41; H, 4.39; N, 17.59; Cl, 22.04.

Step 2—Preparation of 4-Pyridinecarboxaldehyde oxime, methiodide

A solution of 4-pyridinecarboxaldehyde oxime, hydrochloride (24.5 g, 154 mmol) in 250 ml of water was treated with solid sodium bicarbonate (13 g, 155 mmol) and the resulting oil was extracted into 1.2 l of ethyl acetate. The extract was washed with saturated sodium chloride solution, dried over anhydrous magnesium sulfate and calcium sulfate, and concentrated to 500 ml of solution in vacuo. This concentrate was treated with iodomethane (21.5 ml, 344 mmol) and heated with 100 ml of acetonitrile under reflux for two hours. The resulting yellow salt which separated was collected by filtration and dried to provide 35.8 g of 4-pyridinecarboxaldehyde oxime, methiodide, mp 180°-182° C.

Step 3—Preparation of 1,2,3,6-Tetrahydro-1-methyl-4-pyridinecarboxaldehyde, oxime A solution of 4-pyridine carboxaldehyde, oxime, methiodide (35.5 g, 134 mmol) in 150 ml 50% aqueous methanol was added dropwise to a cooled solution of sodium borohydride (8.84g 234 mmol) in 150 ml of 50% aqueous methanol such that the temperature was 0° C. ±5° C. After the mixture was stirred three days at room temperature, it was filtered and the filtrate was concentrated to 150 ml in vacuo. The free base, containing some inorganic salts, was collected by filtration. A portion of the free base (3.15 g) was dissolved in 100 ml of hot ethyl acetate, filtered to clarify, and the cooled filtrate treated with gaseous hydrogen chloride to provide 2.6 g of 1,2,3,6-tetrahydro-1-methyl-4-pyridine carboxaldehyde oxime hydrochloride, mp 246°-247° C.

Analysis calculated for $C_7H_{12}N_2O\cdot HCl$ (176.65): C, 47.59; H, 7.42; N, 15.86; Cl$^-$, 20.07; Found: C, 47.63; H, 7.37; N, 15.57; Cl$^-$, 19.49.

MS: Parent peak=140.1
IR: Consistent with structure
$^1$H NMR (DMSO): $\delta$=2.5 (m, 2 +DMSO), 2.8 (s, 3), 3.2 (m, 1), 3.4 (m, 1 +HDO), 3.6–4.0 (m, 2), 6.0 (s, 1), 7.8 (s, 1), 11.2 (s, 1), 11.3 (broad s, 1) ppm $^{13}$C NMR (DMSO): $\delta$=20.8, 41.5, 48.8, 50.6, 124.2, 130.8, 148.7 ppm

EXAMPLE 10

Preparation of 1,2,3,6-Tetrahydro-1-methyl-4-pyridinecarboxaldehyde, O-acetyloxime A slurry of 1,2,3,6-tetrahydro-1-methyl-4-pyridine, carboxaldehyde oxime (2.25 g, 17.55 mmol) in 50 ml of dry tetrahydrofuran was treated with acetic anhydride (2.2 ml, 23.27 mmol), stirred 18 hours, and filtered. The filtrate was treated with gaseous hydrogen chloride, and the resulting solid collected by filtration was triturated with acetone to provide 2.7 g of 1,2,3,6-tetrahydro-1-methyl-4-pyridine carboxaldehyde, O-acetyl oxime, hydrochloride, mp 160°-161° C.

Analysis calculated for $C_9H_{14}N_2O_2\cdot HCl$ (218.69): C,49.43; N, 6.91; N, 12.81; Cl$^-$, 16.21; Found: C, 49.23; H, 7.01; N, 12.63; Cl$^-$, 16.28 .

MS: Parent peak=183
IR: 1780 cm$^{-1}$
$^1$H NMR (DMSO): $\delta$=2.15 (s, 3), 2.6 (m, 2), 2.8 (s, 3), 3.1–3.6 (m, 2 +HDO), 3.9 (m, 2), 6.45 (s, 1), 8.35 (s, 1), 11.5 (s, 1) ppm
$^{13}$C NMR (DMSO): $\delta$=19.3, 20.5, 41.5, 48.5, 50.8, 129.2, 132.2, 156.6, and 168.2 ppm

EXAMPLE 11

Preparation of 1-(1,2,3,6-Tetrahydro-1-methyl-4-pyridinyl)ethanone oxime

Step 1—Preparation of 1-(4-Pyridinyl)ethanone oxime

A solution of 1-(4-pyridinyl)ethanone (200 g, 1.65 mol) and hydroxylamine hydrochloride (125 g, 1.80 mol) in 1 l of methanol was heated under reflux for 24 hours. The reaction mixture was concentrated to 500 ml and the resulting crystals were collected by filtration to give 226 g of the hydrochloride salt of the title compound. This material was dissolved in 500 ml of water, basified carefully with potassium carbonate, and the resulting solid collected and dried to give 1-(4-pyridinyl)ethanone oxime (134 g), mp 154°-155° C.

Step 2—Preparation of 1-(4-Pyridinyl)ethanone oxime, methiodide

A slurry of 1-(4-pyridinyl)ethanone oxime (47.5 g, 349 mmol) and iodomethane (43.2 ml, 698 mmol) in 600 ml acetonitrile was heated under reflux for one hour and filtered warm to collect 89.69 g of 1-(4-pyridinyl)ethanone, oxime, methiodide, mp 192°-193° C.

Step 3—Preparation of 1-(1,2,3,6-Tetrahydro-1-methyl-4-pyridinyl)ethanone oxime A solution of 1-(4-pyridinyl)ethanone oxime, methiodide (48.36 g, 174 mmol) in 200 ml of 50% aqueous methanol was added to a cooled (−5° C.) slurry of sodium borohydride (12.86 g, 340 mmol) in 200 ml 50% aqueous methanol and the reaction mixture was stirred one hour. After some inorganic material was removed by filtration, the methanol was distilled off the filtrate in vacuo. The resulting solid was collected by filtration and dried to provide 1-(1,2,3,6-tetrahydro-1-methyl-4-pyridinyl)ethanone oxime (18 g), mp 166°-168° C.

EXAMPLE 12

Preparation of 1-(1,2,3,6-Tetrahydro-1-methyl-4-pyridinyl)ethanone, O-Methyloxime

Step 1—Preparation of 1-(4-Pyridinyl)ethanone, O-methyloxime

A mixture of 1-(4-pyridinyl)ethanone (25 g, 207 mmol) and methoxylamine hydrochloride (19 g, 227 mmol) was heated under reflux three hours in 100 ml of methanol and then concentrated in vacuo to a solid. The solid was treated with aqueous sodium bicarbonate until a pH of 7 and the separated free base was extracted into 1 l of chloroform. The extract was dried over magnesium sulfate and concentrated in vacuo to provide the O-methyloxime as an oil. This material (31 g, 207 mmol) was dissolved in 200 ml of ethyl acetate, treated with iodomethane (26 ml, 420 mmol), and stirred 18 hours. The resulting bright yellow solid was collected by filtration, washed with ethyl acetate and ethyl ether, and dried to provide 1-(4-pyridinyl)ethanone, O-methyloxime, methiodide, mp 148°–152° C.

$^1$H NMR (DMSO): $\delta$, 2.3 (s, 3), 3.2 (HDO), 4.05 (s, 3), 4.3 (s, 3), 8.2 (d, 2), 9.0 (d, 2) ppm

Step 2—Preparation of 1-(1,2,3,6-Tetrahydro-1-methyl-4-pyridinyl)ethanone, O-methyloxime A solution of 1-(4-pyridinyl)ethanone, O-methyloxime, methiodide (39.5 g, 135 mmol) in 200 ml of 50% aqueous methanol was added dropwise to a cooled (0° C.) solution of sodium borohydride (10.22 g, 270 mmol) in 200 ml of 50% aqueous methanol such that the temperature was less than 0° C. The reaction mixture gradually warmed to room temperature and was stirred for 18 hours. After some insoluble salts were filtered off, the methanol was distilled and the product was extracted into 1 l of ethyl acetate. The extract was washed with a saturated aqueous solution of sodium chloride, dried over magnesium sulfate, and concentrated in vacuo to give 20.85 g of the free base as an oil.

A solution of the base (3 g) in ethyl ether was filtered and the filtrate treated with hydrogen chloride gas to give 2.6 g of 1-(1,2,3,6-tetrahydro-1-methyl-4pyridinyl)ethanone, O-methyloxime hydrochloride, mp 194°–196° C.

Analysis calculated for $C_9H_{16}N_2O \cdot HCl$ (204.71): C, 52.80; H, 8.37; N, 13.69; Cl$^-$, 17.32; Found: C, 52.16; H, 8.38; N, 13.33; Cl$^-$, 17.19.

MS: Parent peak=169

$^1$H NMR (CDCl$_3$): $\delta$=1.9 (s, 3), 2.8 (m, 1), 2.9 (2S+m, 3), 3.0–3.1 (m, 1), 3.5 (m, 1), 3.6 (m, 1), 3.9 (s, 3), 4.1 (m, 1), 5.9 (s, 1), 12.6 (s, 1) ppm $^{13}$C NMR (DMSO): 10.0, 21, 41.0, 49.0, 50.7, 121.7, 131.8, 153.25 ppm

EXAMPLE 13

Preparation of 1-(1,2,3,6-Tetrahydro-4-pyridinyl)ethanone, O-Methyloxime

A solution of 1-(1,2,3,6-tetrahydro-1-methyl-4pyridinyl)ethanone, O-methyloxime (3 g, 17.8 mmol) in 20 ml dry dichloromethane was cooled to 0° C., treated dropwise with 1-chloroethylchloroformate (2.55 g, 17.8 mmol), and stirred 18 hours at room temperature. The reaction mixture was then concentrated in vacuo to an oil which was heated under reflux one hour in 50 ml of methanol. The methanol was distilled off and the residue was chromatographed over silica gel eluting with 5% methanol in ethyl acetate. The desired fractions were combined, concentrated in vacuo, and treated with methanolic hydrogen chloride to give 1.75 g of 1-(1,2,3,6-tetrahydro-4-pyridinyl)ethanone, O-methyloxime hydrochloride, mp 185°–186° C.

Analysis calculated for $C_8H_{14}N_2O \cdot HCl$ (190.68): C, 50.39; H, 7.93; N, 14.69; Cl$^-$, 18.59; Found: C, 50.45; H, 8.03; N, 14.75; Cl$^-$, 18.72.

MS: Parent peak=155

$^1$H NMR (DMSO): $\delta$=1.95 (s, 3), 2.5 (m, 2+DMSO), 3.2 (t, 2), 3.3 (s, HDO), 3.75 (crude q, 2), 6.1 (crude t, 1), 9.3 (broad s, 2) ppm

EXAMPLE 14

Preparation of 1,2,3,6-Tetrahydro-1-methyl-4-pyridinecarboxaldehyde, O-Methyloxime

Step 1—Preparation of 4-Pyridine carboxaldehyde, O-methyloxime

A solution of 4-pyridine carboxaldehyde (15 g, 140 mmol) in 50 ml of methanol was treated with methoxylamine hydrochloride (11.70 g, 141 mmol) and was stirred three days. The resulting crystalline salt was collected by filtration and dried, mp 238°–239° C. The salt was dissolved in 200 ml of water, basified with sodium bicarbonate, and the resulting oil extracted into chloroform. The extract was dried over MgSO$_4$ and concentrated to an oil which was used without further characterization in the next step.

Step 2—Preparation of 4-Pyridinecarboxaldehyde, O-methyloxime, methiodide

A mixture of 4-pyridine carboxaldehyde, O-methyloxime (18.78 g, 140 mmol), and iodomethane (17.4 ml, 280 mmol) was heated under reflux in 200 ml of acetonitrile one hour. The reaction mixture was concentrated to half volume in vacuo and the resulting yellow crystals were collected and dried to provide 28.64 g of 4-pyridinecarboxaldehyde, O-methyloxime, methiodide, mp 173°–175° C.

Analysis calculated for $C_8H_{11}N_2OI$ (278.10): C. 34.55, H, 3.99, N, 10.08; Found: C, 34.43, H, 3.96, N, 9.97.

Step 3—Preparation of 1,2,3,6-Tetrahydro-1-methyl-4-pyridinecarboxaldehyde, O-methyloxime A solution of 4-pyridine carboxaldehyde, O-methyloxime methiodide (32.78 g, 118 mmol) in 150 ml 50% aqueous methanol was added dropwise to a solution of sodium borohydride (7.79 g, 206 mmol) in 150 ml of aqueous 50% methanol keeping the temperature 0° C. ±5° C. After the solution was stirred one hour, some of the inorganic salts were removed by filtration and the filtrate was concentrated to a mass of oily crystals in vacuo. A portion (4.5 g) of this material was partially dissolved in boiling ethyl ether, filtered, and the filtrate treated with hydrogen chloride to give 1,2,3,6-tetrahydro-1-methyl-4-pyridine carboxaldehyde, O-methyloxime, hydrochloride (2.35 g), mp 212°–214° C.

Analysis calculated for $C_8H_{14}N_2O \cdot HCl$ (194.28): C, 49.6; H, 7.99; N, 14.41; Cl$^-$, 18.25; Found: C, 49.62; H, 8.10; N, 14.02; Cl$^-$, 18.21

MS: Parent peak=155

$^{13}$C NMR (DMSO): δ=20.7, 41.5, 48.7, 61.5, 126.4, 130.0, 149.1 ppm $^{1}$H NMR (DMSO): δ=2.5 (m, 2 +DMSO), 2.8 (s, 3), 3.2 (broad s, 1), 3.5(broad s +s, 1 +HDO), 3.8 (m +s, 5), 6.2 (s, 1), 7.9 (s, 1), 11.1 (s, 1) ppm

EXAMPLE 15

Preparation of 1,2,3,6-Tetrahydro-4-pyridinecarboxaldehyde, O-Methyloxime

A slurry of 1,2,3,6-tetrahydro-1-methyl-4-pyridine carboxaldehyde, O-methyloxime hydrochloride (4.93 g, 60% pure by microanalysis, contaminated with inorganic salts, 16.6 mmol of base) in 75 ml dry CH$_2$Cl$_2$ was treated with 2.3 ml of triethylamine (18 mmol) stirred one hour, and then treated with 2.2 ml (20 mmol) of 1-chloroethyl chloroformate. After the mixture was stirred 18 hours under nitrogen, the mixture was concentrated in vacuo to an oily sludge and flash chromatographed over silica gel eluting with ethyl acetate. The desired fractions were combined and concentrated to an oil which was heated under reflux in 100 ml of methanol for two hours. The reaction mixture was diluted with 100 ml ethyl acetate, treated with hydrogen chloride gas, and slowly concentrated to half-volume and cooled. Needles of 1,2,3,6-tetrahydro-4-pyridinecarboxaldehyde, O-methyloxime, hydrochloride (1.2 g), mp 247° C., were collected by filtration and dried.

Analysis calculated for C$_7$H$_{12}$N$_2$O.HCl (176.65): C, 47.59; H, 7.42; N, 15.86; Cl$^-$, 20.07 ; Found: C, 47.65; H, 7.29; N, 15.81; Cl$^-$, 20.02.

MS: Parent peak=139.1

$^{13}$C NMR (DMSO): 20.0, 40.8, 41.1, 61.5, 127.0, 130.3, 149.5 ppm $^{1}$H NMR (DMSO): δ=2.5 (m, under DMSO, 2), 3.2 (t, 2), 3.4 (s, HDO), 3.75 (broad s, 2), 3.8 (s, 3), 6.1 (s, 1), 7.9 (s, 1), 9.6 (broad s, 2) ppm

We claim:

1. A compound having the formula

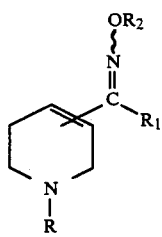

I wherein

R is
  hydrogen or alkyl from one to six carbon atoms;
R$_1$ is
  hydrogen;
  alkyl of from one to six carbon atoms optionally substituted with hydroxy or alkoxyl of from one to four carbon atoms;
  alkenyl of from one to six carbon atoms optionally substituted with hydroxy or alkoxyl of from one to four carbon atoms;
  alkynyl of from one to six carbon atoms optionally substituted with hydroxy or alkoxyl of from one to four carbon atoms;
  cycloalkyl of from three to eight carbon atoms;

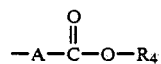

where A is a bond or is a hydrocarbon chain of from one to four carbon atoms and when containing two or more carbon atoms may contain one double bond and where R$_4$ is alkyl of from one to six carbon atoms;

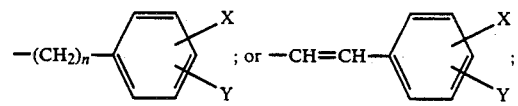

where n is zero to four and X and Y are independently selected from
  hydrogen,
  fluorine,
  chlorine,
  bromine,
  hydroxy,
  alkyl of from one to three carbon atoms, or
  alkoxyl of from one to four carbon atoms;
R$_2$ is
  alkyl of from one to six carbon atoms optionally substituted with hydroxy or alkoxyl of from one to four carbon atoms;
  alkenyl of from one to six carbon atoms optionally substituted with hydroxy or alkoxyl of from one to four carbon atoms;
  alkynyl of from one to six carbon atoms optionally substituted with hydroxy or alkoxyl of from one to four carbon atoms;
  cycloalkyl of from three to six carbon atoms; or

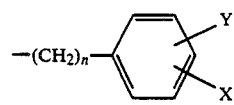

where n is zero to four and X and Y are independently selected from
  hydrogen,
  fluorine,
  chlorine,
  bromine,
  hydroxy,
  alkyl of from one to three carbon atoms, or
  alkoxyl of from one to four carbon atoms;
  alkylcarbonyl of from two to twelve carbon atoms;
  alkenylcarbonyl of from three to twelve carbon atoms;
  alkynylcarbonyl of from three to twelve carbon atoms;

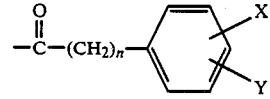

or

-continued

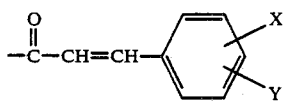

where n, X and Y are as previously defined; or

where $R_5$ and $R_6$ are independently selected from hydrogen, alkyl of from one to four carbon atoms or phenyl;

or a pharmaceutically acceptable acid addition salt thereof;

with the provisos that when R is methyl, $R_1$ is hydrogen; and when R is ethyl, and $R_1$ is hydrogen, $R_2$ may not be acetyl.

2. A compound having the formula

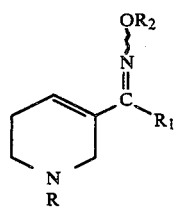

wherein $R_1$ and $R_2$ are as defined in claim 1.

3. A compound having the formula

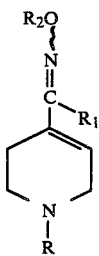

Wherein $R_1$ and $R_2$ are defined in claim 1

4. A compound as defined by claim 1 wherein R is hydrogen.

5. A compound as defined by claim 1 wherein R is alkYl of from one to six carbon atoms.

6. A compound as defined by claim 1 wherein $R_1$ is selected from
straight or branched alkyl of from one to six carbon atoms optionally substituted with hydroxy or alkoxyl of from one to four carbon atoms;
straight or branched alkenyl of from one to six carbon atoms optionally substituted with hydroxy or alkoxyl of from one to four carbon atoms;
straight or branched alkynyl of from one to six carbon atoms optionally substituted with hydroxy or alkoxyl of from one to four carbon atoms; or
cycloalkyl of from three to eight carbon atoms.

7. A compound as defined by claim 1 wherein $R_1$ is

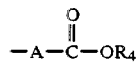

where A is a bond or is a hydrocarbon chain of from one to four carbon atoms and when containing two or more carbon atoms may contain one double bond and $R_4$ is alkyl of from one to six carbon atoms.

8. A compound as defined by claim 1 wherein $R_2$ is selected from
straight or branched alkyl of from one to six carbon atoms optionally substituted with hydroxy or alkoxyl of from one to four carbon atoms;
straight or branched alkenyl of from one to six carbon atoms optionally substituted with hydroxy or alkoxyl of from one to four carbon atoms;
straight or branched alkynyl of from one to six carbon atoms optionally substituted with hydroxy or alkoxyl of from one to four carbon atoms; or
cycloalkyl of from three to eight carbon atoms.

9. A compound as defined by claim 1 wherein $R_2$ is selected from

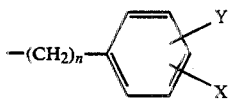

where n is zero to four and X and Y are independently selected from
hydrogen,
fluorine,
chlorine,
bromine,
hydroxy,
straight or branched alkyl of from one to three carbon atoms, or
alkoxyl of from one to four carbon atoms.

10. A compound as defined by claim 1 wherein $R_2$ is selected from
alkylcarbonyl of from two to twelve carbon atoms;
alkenylcarbonyl of from three to twelve carbon atoms; or
alkynylcarbonyl of from three to twelve carbon atoms.

11. A compound as defined by claim 1 wherein $R_2$ is selected from

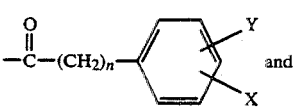 and

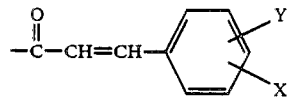

where n, X and Y are as defined in claim 1.

12. A compound as defined by claim 1 wherein $R_2$ is

where $R_5$ and $R_6$ are independently selected from hydrogen and alkyl of from one to four carbons or phenyl.

13. A compound in accordance with claim 2 having the name 1,2,5,6-tetrahydro-3-pyridinecarboxaldehyde, O-methyloxime.

14. A compound in accordance with claim 2 having the name 1,2,5,6-tetrahydro-3-pyridinecarboxaldehyde, O-ethyloxime.

15. A compound in accordance with claim 2 having the name 1-(1,2,5,6-tetrahydro-3-pyridinyl)ethanone, O-methyloxime.

16. A compound in accordance with claim 2 having the name 1-(1,2,5,6-tetrahydro-3-pyridinyl)-1-propanone, O-methyloxime.

17. A compound in accordance with claim 2 having the name 1,2,5,6-tetrahydro-1-methyl-3-pyridinecarboxaldehyde, O-methyloxime.

18. A compound in accordance with claim 2 having the name 1,2,5,6-tetrahydro-1-methyl-3-pyridinecarboxaldehyde, O-ethyloxime.

19. A compound in accordance with claim 2 having the name 1,2,5,6-tetrahydro-1-ethyl-3-pyridinecarboxaldehyde, O-methyloxime.

20. A compound in accordance with claim 3 having the name 1,2,3,6-tetrahydro-4-pyridinecarboxaldehyde, O-methyloxime.

21. A compound in accordance with claim 3 having the name 1-(1,2,3,6-tetrahydro-4-pyridinyl)ethanone, O-methyloxime.

22. A compound in accordance with claim 3 having the name 1,2,3,6-tetrahydro-1-methyl-4-pyridine carboxaldehyde, O-methyloxime 23. A compound in accordance with claim 3 having the name 1,2,3,6-tetrahydro-1-methyl-4-pyridinecarboxaldehyde, O-acetyl oxime.

24. A pharmaceutical composition useful for alleviating pain in a mammal comprising an analgesically effective amount of a compound as defined in claim 1 together with a pharmaceutically acceptable carrier.

25. A pharmaceutical composition useful for the treatment of the symptoms of cognitive decline in an elderly patient comprising a cholinergically effective amount of a compound as defined in claim 1 in combination with a pharmaceutically acceptable carrier.

26. A method of alleviating pain in a mammal comprising administering to a mammal in need of such treatment an analgesically effective amount of a compound in accordance with claim 1 together with a pharmaceutically acceptable carrier.

27. A method of treating the symptoms of cognitive decline in an elderly patient comprising administering to patient in need of such treatment a cholinergically effective amount of a compound as defined in claim 1 in combination with a pharmaceutically acceptable carrier.

* * * * *